United States Patent [19]

Kalvinsh et al.

[11] 4,451,485

[45] May 29, 1984

[54] TREATMENT OF CARDIO-VASCULAR DISEASES WITH 3-(2,2,2-TRIMETHYLHYDRAZINIUM) PROPIONATE DIHYDRATE

[75] Inventors: Ivars Y. Kalvinsh, poselok Salaspils; Alexei V. Vinogradov, Moscow; Maris M. Veveris, Riga; Inna I. Makarova, Moscow; Anatoly S. Birman, Riga; Georgy V. Barmotin, Moscow; Oleg N. Akifiev, Riga, all of U.S.S.R.

[73] Assignee: Institu Organicheskogo Sinteza Akademii Nauk Latviiskoi SSR, Riga, U.S.S.R.

[21] Appl. No.: 419,454

[22] Filed: Sep. 17, 1982

[30] Foreign Application Priority Data

Sep. 17, 1981 [SU] U.S.S.R. ............................ 3374766

[51] Int. Cl.³ .................................... A61K 31/205
[52] U.S. Cl. ...................... 424/316; 260/501.13
[58] Field of Search .................................... 424/316

[56] References Cited

PUBLICATIONS

Chemical Abstracts, 94:30198d (1981) [Eremeev et al., PCT Int. Appl. 80 01,068, 5/29/80].
Chemical Abstracts, 94:120876c (1981) [Belgium 880,831, 6/23/80].

Primary Examiner—Richard A. Schwartz
Attorney, Agent, or Firm—Burgess, Ryan & Wayne

[57] ABSTRACT

A pharmaceutical composition for the treatment of cardio-vascular diseases comprising 3-(2,2,2-trimethylhydrazinium) propionate dihydrate of the following formula:

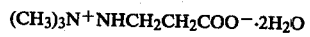

$(CH_3)_3N^+NHCH_2CH_2COO^- \cdot 2H_2O$ and a pharmaceutically acceptable diluent.

4 Claims, No Drawings

TREATMENT OF CARDIO-VASCULAR DISEASES WITH 3-(2,2,2-TRIMETHYLHYDRAZINIUM) PROPIONATE DIHYDRATE

FIELD OF THE INVENTION

The present invention relates to medicine and, more particularly, to a novel pharmaceutical composition for the treatment of cardio-vascular disease such as cardiac insufficiency resulting from valvular defects, myocarditises, cardiosclerosis, ischemic heart disease, rhythm disorders (arrhythmia) of different genesis.

BACKGROUND OF THE INVENTION

At present the principal selective cardiotonic pharmaceutical preparations are cardiac glycosides. They cover preparations of digitalis, as well as lychnis, strophanthus and may lily (cf. M. Yu. Mashkovsky, Pharmaceutical Preparations, M., Meditsina Publishing House, 1977).

The basic disadvantage of glycosides is their low therapeutica index. Overdosage of the preparations causes serious complications including acute bradycardia, polytone extrasystole, bigeminy, trigeminy, deceleration of atrioventricular condition, ventricular flutter and diastolic cardiac arrest.

A disadvantage resides also in the absence of a distinct correlation between the preparation concentration in blood and the effect obtained. Furthermore, glycosides frequently cause irritation of the mucous membrane of the stomach affecting the vomiting center resulting in dyspeptic disturbances.

A large group of preparations for the treatment of cardio-vascular diseases is constituted by antiarrhythmic preparations. One of the most widely employed among them is novocainamide which is successfully administered to treat various kinds of rhythm disturbances including extrasystole. However, even this preparation can cause side effects including general weakness, headache, nausea, vomiting, insomnia, dyspeptic phenomena and, with the intravenous mode of administration, possibly a cardiogenic shock. Furthermore, due to the possible inhibition of myocardial contractibility and reduction of arterial pressure in the case of myocardial infarction, the preparation should be administered with great caution.

A similar disadvantage is inherent in the highly efficient preparations Aimalin and Ethmozin (ethyl ester of 2-carbamic acid 10-(3-morpholylpropionyl)phenothiazino hydrochloride) which also lower contractile properties of the myocardium thus causing a reduction of arterial pressure and complicating their administration because of cardiogenic shock and hypotension.

β-Adrenoblockers (Ideral, Benzodixin, Oxprenolol) also have a number of negative side effects. These compounds are highly toxic ($LD_{50}$ of Inderal is 30–50 mg/kg for white mice), provide a negative inotropic effect; they are contraindicated for some heart diseases such as sinus bradycardia, atrioventricular block, cardiac insufficiency, bronchial asthma, diabetes mellitus and the like.

To cut short attacks of breast pain use is successfully made of organic nitrates among which nitroglycerin has enjoyed the most extensive application. The latter preparation improves tonus of coronary arteries and adjusts resistance of peripheral vessels, thus facilitating the heart's function of blood discharge into the aorta.

A negative property of nitroglicerin is the short duration of its effect and ability to cause strong cephalalgia due to changing tonus of skull veins.

Also known is a naturally-occurring metabolite γ-butyrobetain featuring a broad range of biological activity including an effect on the cardio-vascular system (Nature, 183,328, 1959). However, γ-butyrobetain is rapidly metabolized in the organism into carnitine and, due to this fact, it possesses only a short-time effect.

SUMMARY OF THE INVENTION

It is an object of the present invention to provide a novel pharmaceutical preparation for the treatment of cardiovascular diseases which feature low toxicity, higher efficiency and longer effect, and to eliminate side phenomena characteristic of known preparations intended for the treatment of cardio-vascular diseases.

DETAILED DESCRIPTION OF THE INVENTION

The pharmaceutical composition according to the present invention is novel and hitherto unknown in the art.

This object is accomplished by a novel pharmaceutical composition for the treatment of cardio-vascular diseases comprising an 3-(2,2,2-trimethylhydrazinium)-propionate of the following formula:

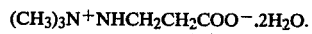

$$(CH_3)_3N^+NHCH_2CH_2COO^-.2H_2O.$$

In combination with a pharmaceutically accepatable diluent composition in the form of an injection, the active ingredient is present in an amount of 5 to 40% by weight and, as the pharmaceutically acceptable diluent, a solvent is used (e.g. distilled water or an isotonic solution).

When administered as tablets or capsules, the composition contains the active ingredient in an amount of 0.1 to 0.5 g per tablet or capsule.

Special experimental studies have shown that the effect of the preparation is based on its ability to dilatate coronary arteries, thus accelerating assimilation, by myocardium, of energy-supplying substances and providing a positive effect on the mitochondrial apparatus of myocardium cells which eventually contributes to a pronounced development of a positive inotropic effect of the cardiac muscle.

The pharmaceutical preparation according to the present invention can be useful in the treatment of such diseases as heart insufficiency, valvular defects, myocarditises, cardiosclerosis, ischemic heart disease, rhythm disturbances of different genesis. In these cases its effect is superior to the therapeutic action of other pharmaceutical preparations including, for example, cardiac glycosides, β-blockers, Carbocromene. Especially pronounced therapeutic results have been observed in the case of chronic decompensation resulting from rheumatic valvular defects and acute circulatory insufficiency resulting from myocardial infarction. Also positive, though less pronounced, effects are observed upon administration of the pharmaceutical preparation according to the present invention in the case of paroxysmal tachycardia, fibrillation, A-V block and paroxysms. The preparation according to the present invention has been tested in experiments on animals and in clinics on patients with various kinds of pathology.

Thus, the effect of the preparation according to the present invention has been studied relative to the variation of arrhythmogenic and lethal doses of calcium chloride. An experiment was carried out on white mice of both sexes weighing 19-28 g which were narcotized by urethane and an ECG was remetered in transthoracic lead. A 2% solution of calcium chloride was administered to the test animals into the tail vein at a constant rate (0.1 ml for 15 seconds). The average dose of calcium chloride causing the appearance of arrhythmia and heart arrest was determined. In the test groups, the studied compounds were administered 45, 60, 120, 180 and 240 minutes before the beginning of administration of calcium chloride (Table 1). It has been found that even a single preliminary administration of the preparation based on 3-(2,2,2-trimethylhydrazinium)-propionate intraperitoneally increases the arrhythmogenic and lethal doses of calcium chloride. Though the prior art preparations novocainamide and quinidine in appropriate doses cause a more pronounced increase of the arrhythmogenic dose of calcium chloride, the preparation according to the present invention results in a longer antiarrhythmic effect at a substantially lower toxicity (Table 2).

The antiarrhythmic activity was studied in experiments on white rats of both sexes with a mass of 190 to 230 g narcotized by urethane. An ECG was recorded for these animals. Into the femoral vein of the rats, aconitine was introduced at a constant rate and its arrhythmogenic and lethal doses were determined along with their variation under the protective effect of the preparation according to the present invention. It has been found that the preparation has a pronounced protective effect also for the peroral mode of administration (Table 3).

Thus, prophylactic peroral administration of the preparation at a daily dose of 25 mg/kg during one week substantially increases the arrhythmogenic and lethal doses of aconitine (by 38.7 and 27.6%, respectively) injected 1-2 hours after the last administration of the preparation of the invention. At a more lasting administration, protective properties of the preparation are pronounced even more clearly (Table 3).

The effect of the preparation according to the present invention on the variation of the arrhythmogenic dose of Strophanthin G was studied in experiments on rabbits of both sexes with a mass of 0.3 to 0.6 kg administered with Strophanthin G at a dose of 60 μg/kg into the marginal auricular vein and, after every 5-10 minutes, at a dose of 5-10 μg/kg until the appearance of a stable ventricular extrasystole. In the test groups 20-30 minutes before administration of the glycoside a solution of 3-(2,2,2-trimethylhydrazinium)propionate was prophylactically administered intravenously. The ECG was recorded in II standard lead.

It was found that at a dose of 10 mg/kg, the preparation increased the arrhythmogenic dose of Strophanthin G from 67±9 to 90±15 μg/kg (Table 4). At a further increase of the dose to the preparation to the present invention, its protective effect was increased too.

TABLE 1

Variation of arrhythmogenic and lethal doses of $CaCl_2$ with time after administration of the studied pharmaceutical compositions in experiments on mice.

| Nos | Pharmaceutical composition | Preventive dose, mg/kg intraperitoneal administration | Time, minutes | | | | | | | | | |
|---|---|---|---|---|---|---|---|---|---|---|---|---|
| | | | 45 | | 60 | | 120 | | 180 | | 240 | |
| | | | arrhythmogenic | lethal | arrhythmogenic | lethal | arrhythmogenic | lethal | arrhythmogenic | lethal | arrhythmogenic | lethal |
| | | | Doses of $CaCl_2$ mg/kg | | | | | | | | | |
| 1 | 2 | 3 | 4 | 5 | 6 | 7 | 8 | 9 | 10 | 11 | 12 | 13 |
| 2 | Injection form of the preparation of the invention, 40% solution of 3-(2,2,2-trimethylhydrazinium) propionate in 0.3% solution of NaCl | 10 30 | 91.5 | 101.7 | 103.4 106.7 | 122.2 122.8 | 111.9 | 130 | 110.1 117.5 | 116 130.2 | 121.9 | 128 |
| 3 | Novocainamide | 10 30 | | | 114.16 125.16 | 120.8 143 | 86.85 93.16 | 104.5 114.9 | | | | |
| 4 | Quinidine | 3 10 | 128.9 120.84 | 147.7 138.54 | 104.5 119.48 | 117.8 126.2 | 87.47 94.5 | 103.65 117.6 | 88.7 | 115.8 | | |
| 5 | Control | — | 85 | 100.9 | | | | | | | | |

TABLE 2

Acute toxicity of pharmaceutical compositions in experiments on white mice at intravenous administration.

| Pharmaceutical composition | $LD_{50}$, mg/kg |
|---|---|
| Injection form of the preparation of this invention, 40% solution of 3-(2,2,2-trimethylhydrazinium) propionate in distilled water | 4,430 (3,164.3–6.202) |
| Novocainamide | 112 (97.39–128.8) |
| Quinidine | 68 (58.6–78.88) |

TABLE 3

Antiarrhythmogenic activity of the preparation according to the present invention after repeated administration in experiments on rats.

| Dose of the pharmaceutical composition (mg/kg) administered perorally and containing, g: | | Aconitine dose variation, % Administration for | | | |
|---|---|---|---|---|---|
| | | 1 week | | 2 weeks | |
| | | Arrhythmogenic | Lethal | Arrhythmogenic | Lethal |
| 3-(2,2,2-trimethylhydrazinium)propionate | 0.4000 | | | | |
| Silica with purity grade of 99.9% and particle size of 5-20 nm | 0.0340 | | | | |
| potato starch | 0.0586 | | | | |
| Methylcellulose | 0.0024 | | | | |
| Magnesium stearate | 0.0050 | | | | |
| 25 | | 38.7 | 27.6 | 42.26 | 24.7 |

TABLE 3-continued

Antiarrhythmogenic activity of the preparation according to the present invention after repeated administration in experiments on rats.

| Dose of the pharmaceutical composition (mg/kg) administered perorally and containing, g: | Aconitine dose variation, % | | | |
|---|---|---|---|---|
| | Administration for | | | |
| | 1 week | | 2 weeks | |
| | Arrhythmogenic | Lethal | Arrhythmogenic | Lethal |
| 100 | 55.6 | 16.2 | 34.6 | 9.7 |

TABLE 4

Variation of the arrhythmogenic dose of Atrophanthin G under the action of the pharmaceutical preparation of the present invention

| Pharmaceutical composition | Preparation dose, mg/kg intravenously | Arrhythmogenic dose of Strophanthin, μg/kg | Duration of arrhythmia, minutes |
|---|---|---|---|
| 10% solution of the preparation according to the present invention containing 3-(2,2,2,-trimethylhydrazinium)propionate as the active ingredient | 10 | 90 ± 15 | 12 ± 6 |
| | 25 | 100 ± 10 | 8 ± 5 |
| | 50 | 106 ± 12 | 15 ± 8 |
| — | — | 67 ± 9 | 20 ± 10 |

To investigate the therapeutic effect of the preparation according to the present invention relative to the Strophanthin arrhythmia, another series of experiments was carried out. Strophanthin was intravenously administered to rabbits of both sexes with a mass of 3.0 to 3.8 kg at a general dose of 80 μg/kg which caused arrhythmia within 40-60 minutes. The test preparation was intravenously administered at the background of arrhythmia in the test group.

It was found that the preparation based on 3-(2,2,2-trimethylhydrazinium)propionate at a dose of 1 to 3 mg/kg in the majority of tests, within 1-2 minutes after the intravenous administration, temporarily arrested ventricular tachyarrhythmia caused by Strophanthin G in rabbits. Changes in the complex QGST were also reduced. After the administration of the preparation at a dose of 5 mg/kg the regular synusal rhythm was retained for 12±5 minutes on the average, whereafter arrhythmia was gradually renewed, but it could be again eliminated by a repeated administration of the preparation at a dose of 2-5 mg/kg. In such cases the sinusal rhythm was retained for 15 to 30 minutes and in the majority of tests arrhythmia never renewed. Furthermore, an experiment was carried out on narcotized guinea pigs with a mass of 600-710 g to which Strophanthin -K was administered into the femoral vein at a total dose of 500 μg/kg.

The preparation based on 3-(2,2,2-trimethylhydrazonium)propionate was intravenously administered against the background of arrhythmia in the test group. It was found that, within 2-3 minutes after the intravenous administration, the test preparation temporarily arrested the ventricular arrhythmia caused by Strophanthin K (see the graph). The changes in the complex QRST were reduced and the atrial fibrillation disappeared which was demonstrated by the appearance of the "p" ripple. In some cases at a timely administration of the preparation in a dose of 2-5 mg/kg it was possible to also eliminate the atrio-ventricular block caused by Strophanthin-K.

The graph illustrates the recording of ECG of a guinea pig.

The effect of compound I on Strophanthin arrhythmia in guinea pigs.

A—ECG of a guinea pig in II standard lead and time mark of 1 second.

B—recording continued.

1—starting ECG

2—ECG 3 minutes after administration of Strophanthin K at a dose of 0.5 mg/kg

3—ECG 2 minutes after administration of the preparation at a dose of 2.0 mg/kg

4—recording of ECG 8 minutes later

5—ECG 3 minutes after administration of the preparation at a dose of 5 mg/kg (18 minutes after the beginning of the experiment)

6—ECG pattern 15 minutes after administration of the preparation at a dose of 5 mg/kg 7—ECG pattern 5 minutes after a repeated administration of the preparation at a dose of 5 mg/kg 8—ECG pattern 45 minutes after the repeated administration of the preparation at a dose of 5 mg/kg.

Furthermore, the preparation according to the present invention was tested for specific antiarrhythmic and antianginal effects. For the purpose of comparison prior art antiarrhythmic preparations were also tested including quinidine, novocainamide, lidocain and a known antianginal agent-carbocromene. The effect of the novel pharmaceutical composition according to the present invention was studied on cats weighing 2.9–3.6 kg. The preparation was used as a 10% aqueous solution containing 3-(2,2,2-trimethylhydrazinium)propionate for the determination of the threshold value of electric fibrillation of auricles and ventricles. Under artificial respiration after opening of the thorax and pericardium, needle-like electrodes were applied to the right auricula and apex of the left ventricle. The irritation was effected by square pulses of 1 m.s., 15 st/s. The current passing through the heart was gradually increased until fibrillations appeared which were evaluated by ECG and arterial pressure on a physiograph available from Narco Bio Systems Co. The studied compounds were administered intravenously. The results thus obtained are shown in Table 5 hereinbelow. It was found that the pharmaceutical composition according to the present invention at dosages of from 6 to 15 mg/kg upon intravenous administration increased by 40–55% the threshold of electrical fibrillation of auricle and ventricles. Novocainamide provided the same effect at dosages of 40–55 mg/kg. Quinidine and lidocain, though exerting their effect at lower doses, had a substantially higher toxicity.

For the comparison of preparations, as the criterion of the range of therapeutic effect, there was used the ratio of the half-lethal dose to the half-effective dose ($LD_{50}/ED_{50}$) which was referred to as the antiarrhythmic index. The antiarrhythmic index of the pharmaceutical composition according to the present invention in the form of a 10% solution containing, as the active ingredient, 3-(2,2,2-trimethylhydrazinium)propionate (443) for this particular type of arrhythmia, was substantially higher than the antiarrhythmic index of quinidine (26), lidocain (13) and novocainamide (2.3). The comparative study of the antiarrhythmic activity of pharmaceutical preparations using an acotine model of arrhythmia was effected in experiments on white rats weighing 190–240 g. The test preparations were administered intraperitoneally 10–40 minutes before administration of aconitine. The results are shown in Table 5 hereinbelow.

From this model of arrhythmia, the pharmaceutical preparation according to the present invention shows a substantially higher activity as compared to the known antiarrhythmic preparations. Thus, the antiarrhythmic index for the pharmaceutical preparation according to the present invention was 354, while for quinidine and novocainamide these values were 16 and 2.5, respectively. As the third model of arrhythmia, there was used strophanthin arrhythmia in guinea pigs. To guinea pigs with a mass of 420 to 710 g Strophanthin-K was administered at a dose of 450 µg/kg. In the control group, this dose of Strophanthin caused the appearance of arrhythmia and death of the animals within 12–20 minutes. Against the background of arrhythmia the test preparations were administered intravenously. The results thus obtained are shown in Table 5 hereinbelow. The tests have shown that the intravenous administration of the pharmaceutical composition according to the present invention and novocainamide cuts short the Strophanthin-induced arrhythmia in guinea pigs for 5–20 minutes in 6 experiments out of 8, whereas the administration of lidocain and quinidine causes improvement, according to ECG data, for only 0.5–3 minutes in 4 out of 7 and in 4 out of 8 animals, respectively.

The study of the preparation according to the present invention for arterial pressure, breathing and hemodynamic effects of norepinephrine, neoepinephrine, novoepinephrine, acetylcholine and histamine was carried out in experiments on cats with a mass of 2.8 to 4.0 kg narcotized by chlorase. There were then recorded the animals' arterial pressure, respiration and ECG on a physiograph produced by Narco Bio-Systems Co.

Hg as compared to the initial value. At the same time, there was observed a short-time increase of the response to histamine (by 5–10%) and change in response to the administration of neoepinephrine (by 5–10%) and acetyl choline (by 10–15%). A further increase of the preparation dose did not cause changes in blood pressure or response to the administration of biogenic amines.

There were also carried out comparative studies of the effect on coronary circulation exerted by the pharmaceutical composition according to the present invention and carbocromene. The pharmaceutical composition according to the invention is used in the form of a 20% injection solution containing 3-(2,2,2-trimethylhydrazinium)propionate as the active ingredient in a 0.9% solution of sodium chloride.

In acute experiments on narcotized cats with a mass of from 2.9 to 4.1 kg under artificial respiration, arterial pressure was recorded in the common carotide artery, central venous pressure in the right auricle, volume rate of blood flow in the ascending aortic arch and volume rate of the coronary blood flow. At the same time, there was recorded the content of oxyhemoglobin in venous coronary blood. The comparative data on the efficiency of the pharmaceutical composition according to the present invention and that of carbocromene are shown in Table 6 hereinbelow.

As it is seen from the Table, the pharmaceutical composition according to the present invention and carbocromene, in equivalent doses, increase, over a long time, the volume rate of coronary blood flow with a low effect exerted on the arterial pressure. Both preparations do not change or only slightly increase the cardiac output. Furthermore, the preparation according to the present invention and carbocromene, lastingly increase saturation of the venous blood of coronary sinus with oxygen, whereas toxicity of the preparation of this in-

TABLE 5

Antiarrhythmic activity and acute toxicity of the test pharmaceutical compositions.

| Nos 1 | Pharmaceutical composition 2 | $ED_{50}$ mg/kg/$LD_{50}$/$ED_{50}$/ | | | Acute toxicity in white mice at intravenous administration, $LD_{50}$ mg/kg |
|---|---|---|---|---|---|
| | | Electric irritation of cat's heart 3 | Aconitine arrhythmia in rats 4 | Strophanthin arrhythmia in guinea pigs | |
| 2 | 10% aqueous solution of the pharmaceutical preparation of this invention for injections containing 3-(2,2,2-trimethylhydrazinium)propionate as the active ingredient | 10 ± 3.5/433/ | 12.5 ± 2.5/354/ | 7.8 ± 2.3/568/ | 4,430 (3,164.3–6,202) |
| 3 | Quinidine | 2.6 ± 0.5/26/ | 4.3 ± 0.6/16/ | 2.3 ± 0.4/30/ | 68 (58.6–78.88) |
| 4 | Novocainamide | 46.0 ± 6.3/2/ | 45.0 ± 5.0/2.5/ | 55.0 ± 7.3/2/ | 112 (97.9–128.8) |
| 5 | Lidocain | 3.0 ± 0.3/13/ | — | 3.8 ± 0.5/11/ | 40 (33.3–48) |

It was found that in doses of 0.5 to 2.0 mg/kg, the preparation administered intravenously did not result in any essential change in arterial pressure, pulse frequency and respiration. The above-specified doses of the preparation did not change changed the level of responses to biogenic amines. At higher doses of the preparation (15–25 mg/kg), there was observed a short-time reduction of arterial pressure by 5–20 mm Hg which in some cases was changed to a more lasting (5–12 minutes) increase of arterial pressure by 5–10 mm vention is 12 times lower than that of carbocromene. For this reason, the therapeutical index of the novel pharmaceutical composition is approximately 3 times higher (314 vs. 130).

There were also carried out tests on the allergenic capacity of the preparation according to the invention, The test results show that the preparation does not cause irritation of vessel walls when administered intravenously; nor does it cause allergic responses for intravenous and peroral modes of administration either upon a single or longtime (up to 30 days) administration thereof.

Doses of up to 10,000 mg/kg of the preparation in experiments on white rats administered perorally on any day of pregnancy caused no embryotoxic or teratogenic effects. The study of the mutagenous activity of the preparation based on 3-(2,2,2-trimethylhydrazinium)propionate dihydrate on fruit flies and salmoneallae has shown that the preparation of the present invention does not have mutagenous activity.

Pharmaceutical preparations based on 3-(2,2,2-trimethylhydrazinium)propionate dihydrate are stable in storage at a temperature of $+5°$ C. for at least two years.

The preparation has been studied on more than 65 patients suffering from various pathology of the cardiovascular systems such as heart rhythm disturbances (arrhythmia) of different etiology, ischemic heart disease, stenocardia, and atherosclerosis.

Although the indications for administration of the preparation were considerably low, during clinical tests it was administered mainly to patients with ischemic heart disease (IHD). Given hereinafter are the results of analysis of the preparation efficiency in 20 men and women aged from 25 to 50 years.

All the patients had typical stenocardia (angina pectoris) attacks, two patients had pronounced pathology of coronary arteries revealed by coronarography and in 5 patients—a large-focus myocardial infarction in anamnesis with pathological O in EGG. All patients were perorally administered with the preparation at a dose of 20 to 40 mg of the active ingredient per kg of bodyweight which each patient was given during the daytime with meals for 4 weeks for a total of 49–96 g on the average per the treatment course.

The following hemodynamic parameters were studied: rate of the heart's beat (RHB), electrocardiogram (ECG), all types of arterial pressure with the curve recording on a Mechanocardiograph 063 (Savitsky's model), beat ejection according to the Wremser-Ranke method, speed of pulse wave propagation, phase analysis of the left ventricle systole on an instrument Mingograph M-34, as well as amplitude time parameters (volume rate of ejection VRE, speed of pressure growth (SPG), rate of heart relaxation (RHR)).

During the investigation, the patients suffering from IHD continued their active way of life, all other medicated compounds were cancelled, except for nitroglycerin tablets when required.

TABLE 6

Hemodynamic characteristics and acute toxicity of the pharmaceutical preparation containing 3-(2,2,2-trimethylhydrazinium)propionate as the active ingredient and the preparation Carbocromene.

| Nos 1 | Pharmaceutical preparation 2 | Dose, mg/kg 3 | Volume rate of arterial pressure, % | | Change of arterial pressure, % 6 | Change of heart output, % 7 | Change of central venous pressure, % 8 | Acute toxicity for white mice at intraperitoneal administration, $LD_{50}$, mg/kg 9 |
|---|---|---|---|---|---|---|---|---|
| | | | Percent of increase 4 | Increase duration, minutes 5 | | | | |
| 2 | 20% injection solution containing 3-(2,2,2-trimethylhydrazinium)propionate as the active ingredient in 0.9% solution of NaCl | 2<br>10<br>25 | 15<br>40<br>55 | 20<br>45<br>70 | 0 + −5<br>±5<br>−8 − +5 | 0 + +5<br>+5 − 10<br>+10 − 20 | 0<br>−5<br>−10 | 7,850<br>(6,541.6 + 9,420) |
| 3 | Carbocromene | 0.5<br>2<br>5 | 30<br>45<br>55 | 35<br>50<br>70 | 0 − −5<br><br>±5<br>0 − +7 | ±5<br><br>+5 − 15<br>+5 − 15 | ±5<br>±5<br>5 − 10 | 650<br>(500 − 845) |

Even during the first week from the beginning of administration of the preparation, a considerable improvement of the patients' state of health was noted: retrosternal pains, occurred less frequently, dyspnea became less pronounced, the rate of administration of nitroglycerin tablets per day was sharply reduced, working capacity was increased, weakness in legs disappeared, heart intermissions became less frequent.

The electrocardiographic investigations revealed a slight decrease of the rate of the heart's beat, disappearance of auricular and ventricular extrasystoles, reinversion of the T ripple and increase of its positive amplitude. In the investigation of arterial pressure there was observed the growth of all types of AP, especially the value of hemodynamic impact which pointed to the growth of kinetic energy of the hemodynamic flow. The growth of the arterial pressure was associated mainly with the increase of beat ejection, whereas the tonus of vessels of elastic and mascular type was not substantially changed which was demonstrated by the values of the propagation speed of the pulse wave.

In the phase analysis of the left ventricle during the treatment, the involution period T was definitely increased, the phase of expulsion E was reduced, the period of tension PT shortened mainly due to a reduction of the period of isometric contraction (IC).

For evaluation of contraction properties of myocardium separately during its systolic and diastolic periods of contraction there were used amplitude-time characteristics rate of heart ejection (RHE), rate of pressure rise (RPR) and rate of heart relaxation (RHR).

The rate of heart ejection (RHE) is determined by the formula: (BV6/E), wherein BV—beat volume in ml, E—time of the expulsion phase in seconds.

The value of RHE characterizes contraction properties of the myocardium during the systole period. An increase of this value in the course of treatment by means of the preparation according to the present invention demonstrates improvement of inotropic properties of myocardium.

The rate of pressure rise is determined by the formula:

$$RPR = \frac{DP - 5}{IC},$$

wherein DP—diastolic pressure in mm, Hg, 5—conventional value of the final diastolic pressure in the aorta, IC—isometric contraction. RPR characterized contractive properties of the myocardium during the period of closed valves and its ability to rapidly surpass the value of pressure in the aorta for opening of the aortic valves.

The rate of heart relaxation (RHR) characterizes activity of the myocardium at the moment of diastole and is determined by the formula $$RHR = \frac{SP - 5}{D},$$

wherein SP—systolic pressure in the brachial artery in mm Hg, 5—conventional value of the final diastolic pressure in the aorta, D—duration of the diastolic period in seconds. The results of the investigation are shown in Table 7 hereinbelow.

The antianginal and antiarrhythmic effects of the preparation according to the present invention were evaluated with the use of the injection pharmaceutical form of the preparation administered intravenously in an amount of 0.2 to 0.4 g based on the active ingredient. In 8 cases of stenocardia attack in 5 patients the preparation rapidly cut short retrosternal pains without any additional administration of nitrates, analgetics and narcotics. However, the analgesic effect was not always stable which necessitated a repeated administration of the preparation.

The preparation efficiency in the case of extrasystolic arrhythmia was studied on 7 patients.

TABLE 7

Variation of hemodynamic parameters in patients with IHD under the effect of (M ± m) of the peroral form of the pharmaceutical composition containing 3-(2,2,2-trimethylhydrazinium)propionate dihydrate as the active ingredient

| Nos | Parameter | before treatment | Parameter during the treatment | | | |
|---|---|---|---|---|---|---|
| | | | 1st week | 2nd week | 3rd week | 4th week |
| 1 | 2 | 3 | 4 | 5 | 6 | 7 |
| 2 | heart rate beat/min | 72.3 + 1.5 | 67.8 + 1.8 | 64.3 + 1.3* | 60.1 + 1.6+ | 62.2 + 1.4* |
| 3 | beat volume, l/min | 70.2 + 5.4 | 72.2 + 3.7 | 74.4 + 4.7 | 80.6 + 4.5 | 84.0 + 3.4* |
| 4 | minute blood volume, l/min | 5.6 + 0.3 | 4.9 + 1.3 | 4.8 + 5.1 | 4.8 + 3.7 | 5.2 + 3.5 |
| 5 | final systolic pressure, mm/Hg | 130.4 + 2.0 | 134.6 + 1.6 | 143.5 + 1.8* | 145.0 + 2.4* | 150.6 + 2.7* |
| 6 | lateral systolic pressure | 115.8 + 0.5 | 116.4 + 2.1 | 118.9 + 1.7 | 120.1 + 1.4* | 125.6 + 0.7* |
| 7. | average dynamic pressure | 89.7 + 1.2 | 90.6 + 0.7 | 91.2 + 1.2 | 92.0 + 1.8 | 92.2 + 1.0 |
| 8 | distolic pressure | 68.2 + 0.6 | 69.9 + 1.3 | 70.3 + 0.9 | 72.3 + 1.4 | 72.0 + 1.8* |
| 9 | pulse pressure | 47.6 + 0.6 | 46.5 + 1.1 | 48.6 + 1.6 | 47.8 + 1.4 | 53.6 + 1.2* |
| 10 | hemodynamic impact | 14.6 + 1.2 | 18.2 + 1.0* | 24.6 + 0.7* | 24.9 + 1.5* | 25.0 + 0.7* |
| 11 | involution period | 830 + 26 | 873 + 33 | 933 + 42* | 1000 + 42* | 965 + 21* |
| 12 | expulsion phase, milliseconds | 222 + 4 | 225 + 2 | 230 + 3 | 232 + 4 | 235 + 3* |
| 13 | tension period, milliseconds | 109 + 4 | 104 + 2 | 100 + 4 | 99 + 3* | 88 + 2* |
| 14 | asynchron. contraction | 56 + 2 | 55 + 4 | 54 + 2 | 56 + 4 | 55 + 3 |
| 15 | isometric contraction, millisec. | 53 + 2 | 49 + 3 | 46 + 4 | 43 + 2* | 33 + 2* |
| 16 | diastol., milliseconds | 499 + 14 | 543 + 21 | 603 + 21* | 669 + 14* | 642 + 14* |
| 17 | volume of heart ejection, ml/sec | 315 + 15 | 320 + 23 | 322 + 13 | 374 + 14* | 357 + 17* |
| 18 | rate of pressure raise, mm Hg/sec | 1,188 + 30 | 1,326 + 45 | 1,473 + 130 | 1,581 + 54* | 2,030 + 68* |
| 19 | rate of heart relaxation, mm Hg/sec | 250 + 9 | 238 + 10 | 229 + 8 | 209 + 8 | 226 + 12 |

Note:
*certainty of difference P ≦ 0.01.

The intravenous administration of the preparation (1 ml of a 40% solution) arrested the rhythm disorder for 5-20 minutes.

Therefore, the pharmaceutical preparation based on 3-(2,2,2-trimethylhydrazinium)propionate in patients with verified ischemic disease provides an inotropic effect on the myocardium, removes retrosternal pains and rhythm disorders such as extrasystole.

Consequently, the pharmaceutical preparation according to the present invention features a special scope of activity: it manifests itself as a vasodilative preparation relative to coronary arteries, facilitates improvement of the myocardial metabolism and possesses a clearly pronounced and stable positive inotropic effect.

The pharmaceutical preparation according to the present invention is preferably administered in the form of injection solutions, tablets, capsules, powders. It is indicated at the rate of 10 to 60 mg/kg of bodyweight as tablets or capsules per day simultaneously with taking meals, or in the form of 10–40% injection solutions. The preparation of the present invention relates to low-toxic substances (List B or even less strict).

Pharmaceutical forms of the preparation for peroral administration are stable for two years at room temperature and are to be stored in a dry, light-protected place. Injection solutions should be stored for not more than 2 years at a temperature of not more than +5° C.

The active ingredient according to the present invention, viz. 3-(2,2,2-trimetylhydrazinium)propionate is prepared by any conventional method; for example, a solution of methyl-3-(2,2,2-trimethylhydrazinium)propionate chloride in water is passed through a column with an ion-exchange resin Amberlite IRA-400/Registered Trade Mark/. The solvent is removed and the residue is crystallized from ethanol. There are thus obtained 140 g (85%) of 3-(2,2,2-trimethylhydrazinium) propionate in the form of colourless crystals with the M.p. of 254°–256° C. PMR spectrum ($\tau$, ppm): 6.79 singlet, $(CH_3)_3N^+$; 6.89 triplet, $CH_2$; 7.77, triplet, $CH_2$.

Found, %: C 39.56, H 10.10, N 15.36; $C_6H_{14}O_2N_2 \cdot 2H_2O$ Calculated, %: C 39.56; H 9.89, N 15.30.

3-(2,2,2-trimethylhydrasinium)propionate dihydrate comprises slightly hygroscopic white substances well soluble in water, hot ethanol and methanol, insoluble in nonpolar solvents, having a weak specific odour. When stored in a closed area at room temperature, it is stable for at 2 years. Upon heating above 40° C. the product loses crystallization water and slowly decomposes.

What is claimed is:

1. A method of treating cardiovascular disease in warm blooded animals comprising administering to said warm blooded animals an effective amount of a composition possessing antiarrhythmic and antianginal activity which comprises the compound 3-(2,2,2-trimethylhydrazinium)propionate dihydrate having the formula:

$$(CH_3)_3N^+NHCH_2CH_2COO^- \cdot 2H_2O$$

and a pharmaceutically acceptable diluent.

2. The method of claim 1 further comprising administering said composition in the form of a tablet, capsule, or powder at the rate of 10 to 60 mg/kg/day.

3. The method of claim 1 further comprising administering said composition in the form of a 10–40% injectable solution.

4. The method of claim 3, wherein the pharmaceutically acceptable diluent is a solvent selected from the group consisting of distilled water and isotonic solution.

* * * * *